(12) United States Patent
Griscik et al.

(10) Patent No.: US 11,517,684 B2
(45) Date of Patent: *Dec. 6, 2022

(54) CAPSULES, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventors: Gregory Griscik, Richmond, VA (US); Raymond W. Lau, Richmond, VA (US); Eric Hawes, Glen Allen, VA (US)

(73) Assignee: Altria Client Services LLC, Richmond, VA (US)

(*) Notice: Subject to any disclaimer, the term of this patent is extended or adjusted under 35 U.S.C. 154(b) by 906 days.

This patent is subject to a terminal disclaimer.

(21) Appl. No.: 16/252,953

(22) Filed: Jan. 21, 2019

(65) Prior Publication Data

US 2020/0229510 A1 Jul. 23, 2020

(51) Int. Cl.
*A24F 47/00* (2020.01)
*A61M 11/04* (2006.01)
*A24B 15/167* (2020.01)
*A61M 15/00* (2006.01)
*A24F 40/46* (2020.01)

(52) U.S. Cl.
CPC ......... *A61M 11/042* (2014.02); *A24B 15/167* (2016.11); *A24F 40/46* (2020.01); *A61M 15/009* (2013.01)

(58) Field of Classification Search
CPC ....... A24F 40/42; A24F 40/46; A61M 11/042; A61M 15/009
See application file for complete search history.

(56) References Cited

U.S. PATENT DOCUMENTS 5,060,671 A * 10/1991 Counts .................... A24F 40/30
131/273
5,093,894 A * 3/1992 Deevi ..................... A24F 40/46
392/404
5,369,723 A * 11/1994 Counts .................... A24D 1/20
131/194

(Continued)

FOREIGN PATENT DOCUMENTS

WO WO-2016/005533 A1 1/2016
WO WO-2016/005601 A1 1/2016
WO WO-2019/005526 A1 1/2019

OTHER PUBLICATIONS

Taking E-Cigarettes Further, E-Vapor Products; https://www.pmi.com/smoke-free-products/mesh-taking-e-cigarettes-further.

(Continued)

*Primary Examiner* — Eric Yaary
(74) *Attorney, Agent, or Firm* — Harness, Dickey & Pierce, P.L.C.

(57) ABSTRACT

A capsule for a heat-not-burn (HNB) aerosol-generating device may include a first heater, a second heater, and a frame sandwiched between the first heater and the second heater, and a cannabinoid-containing material. The frame may define open spaces therein and have a rigidity that is adequate to support the first heater and the second heater. The open spaces within the frame may be interconnected and sized for aerosol-permeability and capillary action.

20 Claims, 9 Drawing Sheets

(56) References Cited

U.S. PATENT DOCUMENTS

| | | | |
|---|---|---|---|
| 5,408,574 A | 4/1995 | Deevi et al. | |
| 9,943,114 B2 | 4/2018 | Batista | |
| 2014/0261490 A1* | 9/2014 | Kane | A24F 40/485 |
| | | | 131/328 |
| 2014/0373857 A1* | 12/2014 | Steinberg | A24F 40/46 |
| | | | 131/329 |
| 2015/0027456 A1 | 1/2015 | Janardhan et al. | |
| 2015/0335070 A1 | 11/2015 | Sears et al. | |
| 2017/0071249 A1 | 3/2017 | Ampolini et al. | |
| 2017/0144827 A1 | 5/2017 | Batista | |
| 2017/0150755 A1 | 6/2017 | Batista | |
| 2017/0156403 A1 | 6/2017 | Gill et al. | |
| 2017/0164657 A1* | 6/2017 | Batista | H05B 3/34 |
| 2017/0181472 A1 | 6/2017 | Batista et al. | |
| 2017/0280769 A1 | 10/2017 | Li et al. | |
| 2017/0347711 A1* | 12/2017 | Litten | A24F 40/485 |
| 2018/0177240 A1* | 6/2018 | Duque | A24F 40/44 |

OTHER PUBLICATIONS

CA International Search Report and Written Opinion for PCT/US2020/012161 dated May 4, 2020.

\* cited by examiner

CAPSULES, HEAT-NOT-BURN (HNB) AEROSOL-GENERATING DEVICES, AND METHODS OF GENERATING AN AEROSOL

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be *cannabis*. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a first heater, a second heater, a frame sandwiched between the first heater and the second heater, and a cannabinoid-containing material. The frame may define open spaces therein and have a rigidity that is adequate to support the first heater and the second heater. The open spaces within the frame may be interconnected and sized for aerosol-permeability and capillary action.

At least one embodiment relates to heaters for a capsule for a heat-not-burn (HNB) aerosol-generating device. In an example embodiment, the heaters may include a first heater and a second heater, and at least one of the first heater or the second heater may be in a form of a mesh. Alternatively, at least one of the first heater or the second heater is in a form of a perforated foil.

At least one embodiment relates to a frame for a capsule for a heat-not-burn (HNB) aerosol-generating device. In an example embodiment, the frame may define a cavity. The cavity may be a through-hole or a recess. An aerosol-forming substrate may be disposed in the cavity of the frame. The aerosol-forming substrate is configured to produce an aerosol when heated by at least one of the first heater or the second heater. The aerosol-forming substrate may be a pre-aerosol formulation or a fibrous material configured to release a compound when heated by at least one of the first heater or the second heater.

At least one embodiment relates to a heat-not-burn (HNB) aerosol-generating device. In an example embodiment, the aerosol-generating device may include a device body, a plurality of electrodes, and a power source. The device body is configured to receive a capsule including a first heater, a second heater, a frame sandwiched between the first heater and the second heater, and a cannabinoid-containing material. The plurality of electrodes are disposed within the device body and configured to electrically contact the first heater and the second heater of the capsule. The power source is configured to supply an electric current to the first heater and the second heater of the capsule via the plurality of electrodes.

At least one embodiment relates to a method of generating an aerosol. In an example embodiment, the method may include electrically contacting a plurality of electrodes with a capsule including a first heater, a second heater, a frame sandwiched between the first heater and the second heater, and a cannabinoid-containing material. Additionally, the method may include supplying an electric current to the first heater and the second heater of the capsule via the plurality of electrodes.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
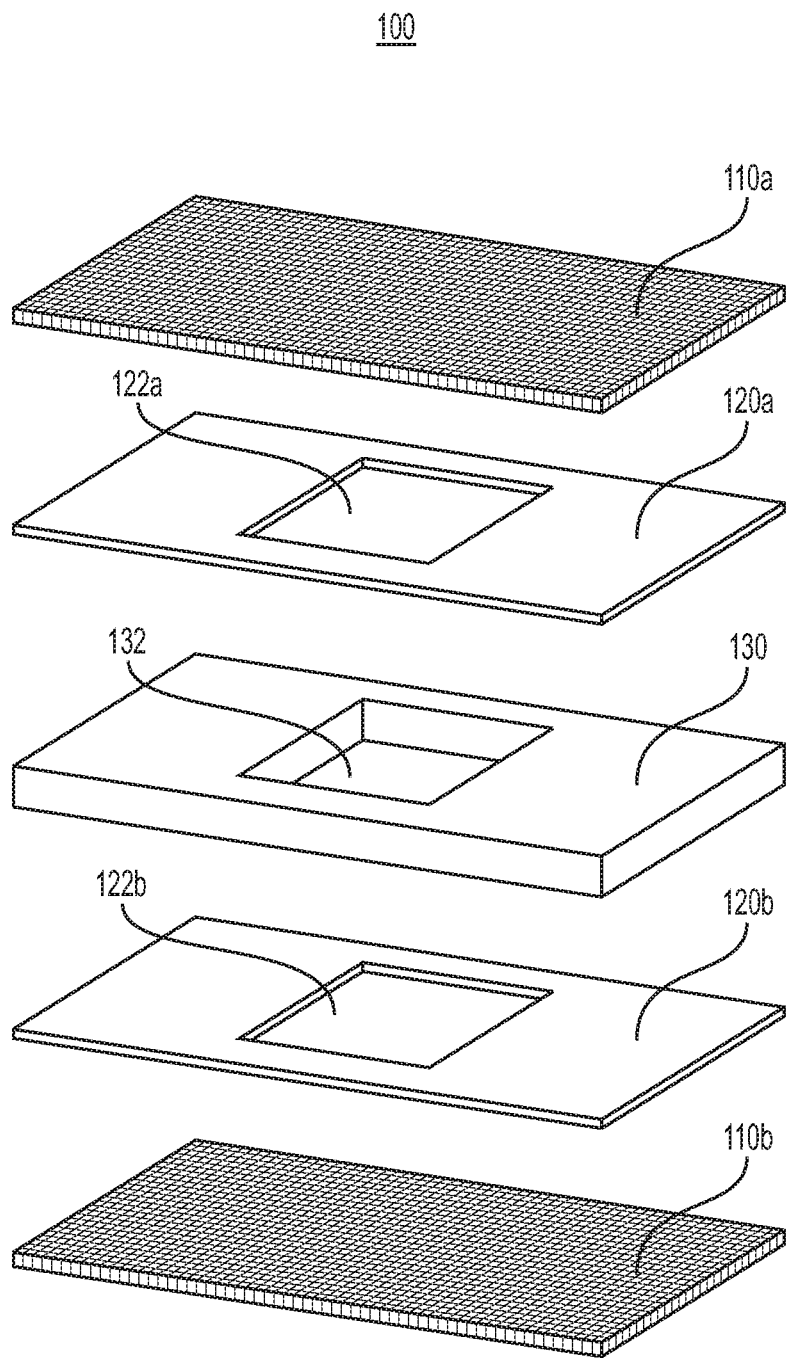
FIG. 1 is an exploded view of a capsule for an aerosol-generating device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements but do not preclude the presence or addition of one or more other features, integers, steps, operations, elements, and/or groups thereof.

When the words "about" and "substantially" are used in this specification in connection with a numerical value, it is intended that the associated numerical value include a tolerance of ±10% around the stated numerical value, unless otherwise explicitly defined.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

FIG. 1 is an exploded view of a capsule for an aerosol-generating device according to an example embodiment. Referring to FIG. 1, a capsule 100 for an aerosol-generating device (e.g., heat-not-burn aerosol-generating device) has a laminar structure and includes a first heater 110a, a second heater 110b, and a frame 130 sandwiched between the first heater 110a and the second heater 110b. As shown, the first heater 110a, the second heater 110b, and the frame 130 have a planar form and a rectangular shape. The first heater 110a, the second heater 110b, and the frame 130 may also be substantially the same size based on a plan view (e.g., ±10% of a given dimension).

However, it should be understood that other sizes, forms, and shapes may be employed for the capsule 100. For instance, the first heater 110a, the second heater 110b, and the frame 130 may have another polygonal shape (regular or irregular), including a triangle, a square, a pentagon, a hexagon, a heptagon, or an octagon. Alternatively, in lieu of being polygonal, the shape may be circular such that the capsule 100 has a disk-like appearance. In other instances, the shape may be elliptical or racetrack-like. The laminar structure and generally planar form of the capsule 100 may facilitate stacking so as to allow a plurality of capsules to be stored in an aerosol-generating device or other receptacle for dispensing a new capsule or receiving a depleted capsule.

The first heater 110a and the second heater 110b are configured to generate heat. As a result, the temperature of the frame 130 may increase during the generation of such heat. In an example embodiment, the first heater 110a and the second heater 110b are configured to undergo Joule heating (which is also known as ohmic/resistive heating) upon the application of an electric current thereto. Stated in more detail, the first heater 110a and the second heater 110b may be formed of conductors (same or different) and configured to produce heat when an electric current passes through the conductors. The electric current may be supplied from a power source (e.g., battery) within an aerosol-generating device. In addition, the electric current from the power source may be transmitted via electrodes configured to electrically contact the first heater 110a and the second heater 110b when the capsule 100 is inserted into the aerosol-generating device. In a non-limiting embodiment, the electrodes may be spring-loaded to enhance an engagement with the first heater 110a and the second heater 110b of the capsule 100. Also, the movement (e.g., engagement, release) of the electrodes may be achieved by mechanical actuation. Furthermore, the supply of the electric current from the aerosol-generating device to the capsule 100 may be a manual operation (e.g., button-activated) or an automatic operation (e.g., puff-activated).

Suitable conductors for the first heater 110a and the second heater 110b include an iron-based alloy (e.g., stainless steel) and/or a nickel-based alloy (e.g., nichrome). In one instance, at least one of the first heater 110a or the second heater 110b is in a form of a mesh. In another instance, at least one of the first heater 110a or the second heater 110b is in a form of a perforated foil (e.g., micro-perforated foil). Thus, the first heater 110a and the second heater 110b may be in a form of a mesh, a perforated foil, or a combination thereof. Furthermore, although two heaters are shown in FIG. 1, it should be understood that, in some example embodiments, only one of the first heater 110a or the second heater 110b may be provided.

The frame 130 is non-conductive and electrically isolates the first heater 110a and the second heater 110b. Additionally, the frame 130 may be configured as an underlying support structure for the capsule 100. In particular, the frame 130 may have a rigidity that is adequate to support its own weight (e.g., so as to not bend in response to gravity when suspended horizontally). The frame 130 may also have a rigidity that is adequate to support the first heater 110a and the second heater 110b such that the capsule 100 maintains a generally planar form after assembly. The thickness of the frame 130 may be about 0.7 mm to about 1.3 mm (e.g., about 1.0 mm), although other dimensions may be suitable based on the design of the capsule 100. As shown in FIG. 1, the frame 130 defines a cavity 132. In a non-limiting embodiment, the cavity 132 is a through-hole.

The frame 130 may be of a solid construction or of a porous construction. In addition, the frame 130 may be constructed from an inert material (e.g., inert relative to an aerosol-forming substrate, such as a pre-aerosol formulation). With regard to a solid construction, the frame 130 may be formed of a polymer (e.g., thermoplastic polymer). Suitable polymers include polyether ether ketone (PEEK), polyethylene (PE), and polypropylene (PP), although example embodiments are not limited thereto. The body (e.g., non-cavity) portion of the frame 130 may optionally be provided with perforations (e.g., micro-perforations) to allow an air flow therethrough, thereby increasing an overall air flow through the capsule 100.

With regard to a porous construction, the frame 130 may be a monolithic structure or a composite structure defining open spaces therein. The open spaces therein may be interconnected and sized so as to provide both aerosol-permeability and capillary action to the porous construction. In a non-limiting embodiment involving a porous construction having a monolithic structure, a single piece of material may define a plurality of pores within (e.g., porous glass). Conversely, in a non-limiting embodiment involving a porous construction having a composite structure, a plurality of pieces of material may be aggregated (e.g., as a compacted material) to define interstices therebetween. As noted supra, the open spaces (e.g., pores and/or interstices) in the above examples are interconnected and configured to be permeable so as to allow air and an entrained aerosol to flow through/from a body (e.g., non-cavity) portion of the frame 130. In addition, like the example involving the solid construction above, the body (e.g., non-cavity) portion of the frame 130 may also be optionally provided with perforations (e.g., micro-perforations) to allow additional air flow therethrough, thereby increasing an overall air flow through the capsule 100. The pores and/or interstices in the above examples are also configured to exert capillary forces when a liquid comes in fluidic communication with the porous construction of the frame 130. As a result, a liquid can optionally be drawn into and retained within the porous construction of the frame 130 by capillary action.

As an example of an aggregated (e.g., compacted) material for the composite structure, the frame 130 may be formed of consolidated fibers. The consolidated fibers may be formed via compression to provide the desired density and porosity. The consolidated fibers used to form the frame 130 may be natural or artificial. The natural fibers may be plant-based fibers (e.g., cellulose fibers). In one instance, the plant-based fibers may be wood fibers consolidated in a form resembling paperboard or cardboard. In another instance, the plant-based fibers may be bast fibers (e.g., *cannabis* fibers). As another example of an aggregated (e.g., compacted) material, the frame 130 may be formed of sintered particles. The sintered particles may include (and are not limited to) sintered ceramic particles (e.g., particles of silica ($SiO_2$), alumina ($Al_2O_3$), and/or zirconia ($ZrO_2$)) and/or sintered plastic particles (e.g., particles of polyether ether ketone (PEEK), polyethylene (PE), and/or polypropylene (PP)).

The capsule 100 may further comprise an aerosol-forming substrate in the cavity 132 of the frame 130. The aerosol-forming substrate may be a cannabinoid-containing material. The aerosol-forming substrate may have various forms. In one instance, the aerosol-forming substrate may be a pre-aerosol formulation. A pre-aerosol formulation is a material or combination of materials that may be transformed into an aerosol. For example, the pre-aerosol formulation may be a liquid, solid, and/or gel formulation including, but not limited to, water, beads, solvents, active ingredients, plant extracts, natural or artificial flavors, and/or aerosol formers. The pre-aerosol formulation in the cavity 132 may include a compound (e.g., cannabinoid), wherein an aerosol including the compound is produced when the pre-aerosol formulation is heated by at least one of the first heater 110a or the second heater 110b. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental. In the present application, aerosol relates to the matter generated or output by the devices disclosed, claimed, and equivalents thereof. In a non-limiting embodiment, the pre-aerosol formulation disposed in the cavity 132 may be in a form of a solid (e.g., wax) that can be contained by the permeable structures of the first heater 110a and the second heater 110b.

In lieu of (or in addition to) the pre-aerosol formulation, the capsule 100 may further comprise a fibrous material in the cavity 132 of the frame 130 as the aerosol-forming substrate (in whole or in part). The fibrous material may be a botanical material. The fibrous material is configured to release a compound when heated by at least one of the first heater 110a or the second heater 110b. The compound may be a naturally occurring constituent of the fibrous material.

For instance, the fibrous material may be a medicinal plant, and the compound released may be a naturally occurring constituent of the plant that has a medically-accepted therapeutic effect. The medicinal plant may be a *cannabis* plant, and the compound may be a cannabinoid. Cannabinoids interact with receptors in the body to produce a wide range of effects. As a result, cannabinoids have been used for a variety of medicinal purposes. The fibrous material may include the leaf and/or flower material from one or more species of *cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis* indica. In some embodiments, the frame 130 may also be formed of *cannabis*. In such an instance, the frame 130 may be formed of *Cannabis sativa*, while the aerosol-forming substrate within the cavity 132 may be formed of *Cannabis* indica (or vice versa), although example embodiments are not limited thereto.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from the first heater 110a and the second heater 110b may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100 (e.g., within the frame 130 and/or the aerosol-forming substrate in the cavity 132), the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100 (e.g., within the frame 130 and/or the aerosol-forming substrate in the cavity 132), the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 100.

Alternatively, the compound may be a non-naturally occurring additive that is subsequently introduced into the fibrous material. In such an instance, the fibrous material may include at least one of cotton, polyethylene, polyester, rayon, combinations thereof, or the like (e.g., in a form of a gauze). In another instance, the fibrous material may be a cellulose material, and the compound introduced may be cannabinoids and/or flavorants by way of plant extracts (e.g., *cannabis* extract). Furthermore, as noted above, a pre-aerosol formulation may be dispersed within the fibrous material.

In FIG. 1, the capsule 100 may further comprise a first adhesive 120a and a second adhesive 120b. The first adhesive 120a is configured to secure the first heater 110a to the frame 130, while the second adhesive 120b is configured to secure the second heater 110b to the frame 130. Additionally, the first adhesive 120a defines a first opening 122a, and the second adhesive 120b defines a second opening 122b. When the capsule 100 is assembled, the first opening 122a and the second opening 122b will align with the cavity 132. As a result, air can flow through the aerosol-forming substrate within the cavity 132 to entrain the aerosol produced when the capsule 100 undergoes heating.

In a non-limiting embodiment, at least one of the first adhesive 120a or the second adhesive 120b is a double-sided tape. In such an instance, a portion of the double-sided tape coinciding with the body (e.g., non-cavity) portion of the frame 130 may optionally be perforated (before or after assembly) to enhance an air flow through the capsule 100. In another instance, at least one of the first adhesive 120a or the second adhesive 120b may be a liquid adhesive. In other instances, the first adhesive 120a and the second adhesive 120b may be omitted in favor of other attachment techniques.

For example, the first heater 110a and/or the second heater 110b may be attached to the frame 130 by ultrasonic bonding, a mechanical fastener, or a combination thereof. One suitable type of mechanical fastener may be a clamshell-type cover (one- or two-piece) which secures the periphery of the first heater 110a and the second heater 110b to the frame 130 while providing an opening that coincides with at least the cavity 132 of the frame 130. Such a clamshell-type cover may have a snap-fit mating arrangement. Alternatively (or in addition), the clamshell-type cover may be amenable to ultrasonic bonding.

Another suitable type of mechanical fastener may be a clip for one or more edges of the capsule 100. The clip may be a resilient clamping structure with a base between two spring-loaded sides/arms. Additionally, the clip may be formed of an insulating material (e.g., plastic). In a non-limiting embodiment, the clip may have a square U cross-section (e.g., square U cross-section with inward-leaning sides/arms when unengaged). In another non-limiting embodiment, the clip may have a triangular cross-section (wherein the sides/arms contact (or almost contact) each other when unengaged) so as to provide a greater gripping force when engaged. The clip may also have an elongated/strip form with a length that corresponds to a majority of the length or width of capsule 100. When assembled, the opposing sides/arms of the clip securely grip the first heater 110a and the second heater 110b to the frame 130. Furthermore, the first heater 110a, the second heater 110b, and/or the frame 130 may abut the base of the clip. A pair of clips may be provided on the two width edges and/or the two length edges of the capsule 100, although example embodiments are not limited thereto.

Figure 2:
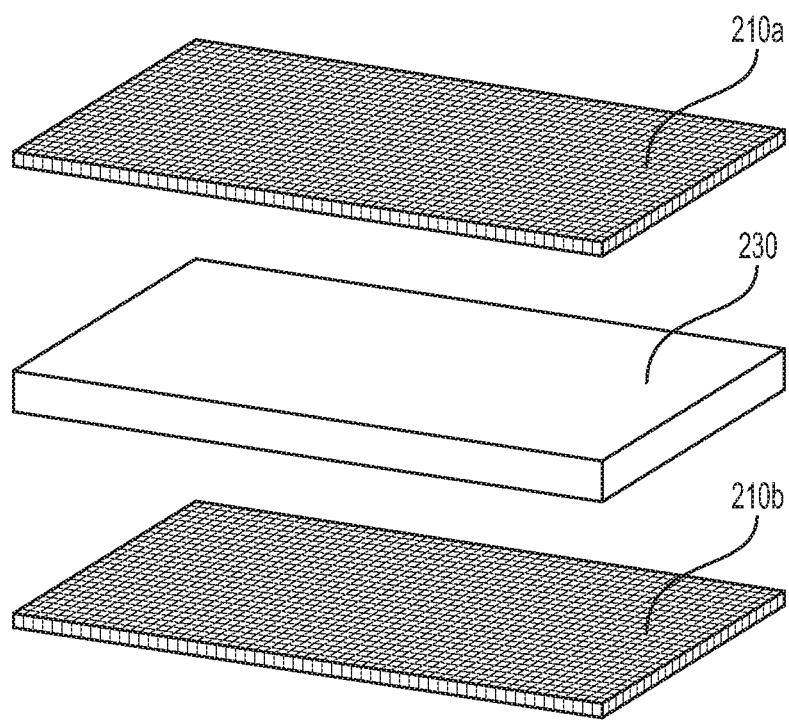
FIG. 2 is an exploded view of another capsule for an aerosol-generating device according to an example embodiment.

FIG. 2 is an exploded view of another capsule for an aerosol-generating device according to an example embodiment. Referring to FIG. 2, a capsule 200 includes a first heater 210a, a second heater 210b, and a frame 230 sandwiched between the first heater 210a and the second heater 210b. The first heater 210a and the second heater 210b may be as discussed above in connection with the first heater 110a and the second heater 110b of FIG. 1 and, thus, the relevant disclosure will not be repeated in the interest of brevity. In FIG. 2, the compound (e.g., cannabinoid) to be heated and released may be integrated with the frame 230. As a result, the frame 230 may be formed entirely of an aerosol-forming substrate (e.g., *cannabis*) such as described with regard to the embodiment of FIG. 1. To facilitate the adequate passage of air through the capsule 200, the frame 230 may have a density in a range of about 0.454 g/cm$^3$ to about 1.361 g/cm$^3$ (e.g., about 0.907 g/cm$^3$). In addition, the porosity may be such that a pressure drop through the frame 230 may in a range of about 5-200 mmH$_2$O (e.g., about 40-100 mmH$_2$O, about 60 mmH$_2$O). The first heater 210a and the second heater 210b may be secured to the frame 230 with any of the options discussed above in connection with securing the first heater 110a and the second heater 110b to the frame 130 of FIG. 1.

Figure 3:
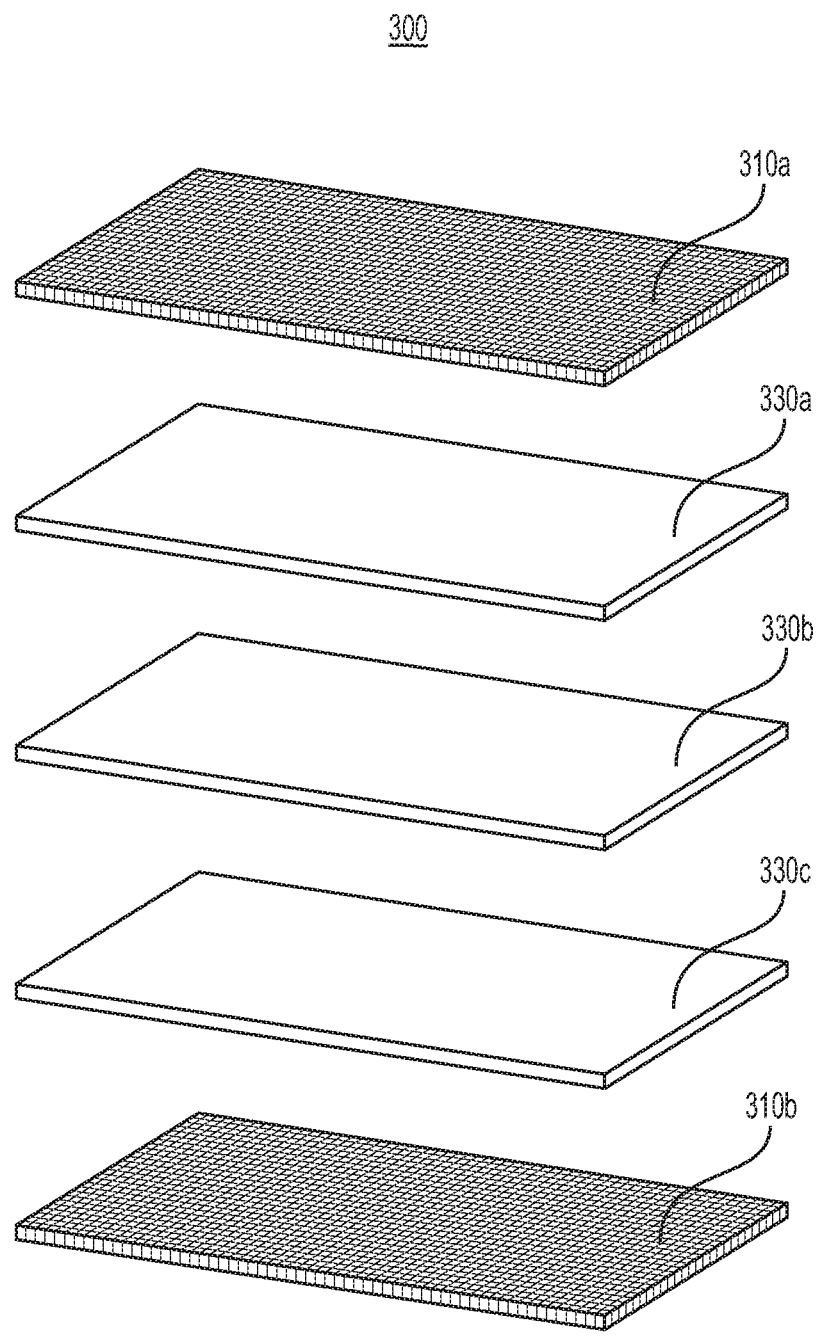
FIG. 3 is an exploded view of another capsule for an aerosol-generating device according to an example embodiment.

FIG. 3 is an exploded view of another capsule for an aerosol-generating device according to an example embodiment. Referring to FIG. 3, a capsule 300 includes a first heater 310a, a second heater 310b, and a frame sandwiched between the first heater 310a and the second heater 310b, wherein the frame is in a form of a multi-layer structure. The multi-layer structure of the frame may include different layers configured to impart distinct flavors. As shown, the multi-layer structure of the frame includes a first frame member 330a, a second frame member 330b, and a third frame member 330c. Each of the first frame member 330a, the second frame member 330b, and the third frame member 330c may have a thickness of about ⅙ mm to about ½ mm (e.g., about ⅓ mm), although example embodiments are not limited thereto.

The first heater 310a and the second heater 310b may be as discussed above in connection with the first heater 110a and the second heater 110b of FIG. 1 and, thus, the relevant disclosure will not be repeated in the interest of brevity. In FIG. 3, the compound (e.g., cannabinoid) to be heated and released may be integrated with the frame. As a result, each of the first frame member 330a, the second frame member 330b, and the third frame member 330c may be formed entirely of an aerosol-forming substrate or other porous construction (e.g., porous glass, sintered particles) with a desired compound dispersed therein.

Additionally, the composition of each of the first frame member 330a, the second frame member 330b, and the third frame member 330c may be the same or different to provide the desired organoleptic appeal. For instance, a different plant material sheet may be used for each of the first frame member 330a, the second frame member 330b, and the third frame member 330c. In such an instance, the first frame member 330a, the second frame member 330b, and the third frame member 330c may be formed of *Cannabis sativa*, *Cannabis indica*, and *Cannabis ruderalis*, respectively. In another instance, the first frame member 330a and the third frame member 330c may be formed of *Cannabis sativa*, while the second frame member 330b may be formed of *Cannabis* indica. In other instances, the first frame member 330a, the second frame member 330b, and the third frame member 330c may have different types and/or amounts of cannabinoids. For example, the first frame member 330a, the second frame member 330b, and the third frame member 330c may include tetrahydrocannabinol (THC), cannabidiol (CBD), cannabinol (CBN), respectively.

To facilitate the adequate passage of air through the capsule 300, each of the first frame member 330a, the second frame member 330b, and the third frame member 330c may have a density in a range of about 0.454 g/cm$^3$ to about 1.361 g/cm$^3$ (e.g., about 0.907 g/cm$^3$). In addition, the porosity may be such that a pressure drop through the first frame member 330a, the second frame member 330b, and the third frame member 330c may in a range of about 5-200 mmH$_2$O (e.g., about 40-100 mmH$_2$O, about 60 mmH$_2$O). The density and/or porosity for each of the first frame member 330a, the second frame member 330b, and the third frame member 330c may also vary individually based on their composition and/or position in order to provide the desired air flow through the capsule 300. Furthermore, the first frame member 330a, the second frame member 330b, and/or the third frame member 330c may be perforated to enhance the air flow through the capsule 300. The size, placement, and quantity of the perforations can be varied for each of the first frame member 330a, the second frame member 330b, and/or the third frame member 330c. The first heater 310a and the second heater 310b may be secured to the frame with any of the options discussed above.

Figure 4:
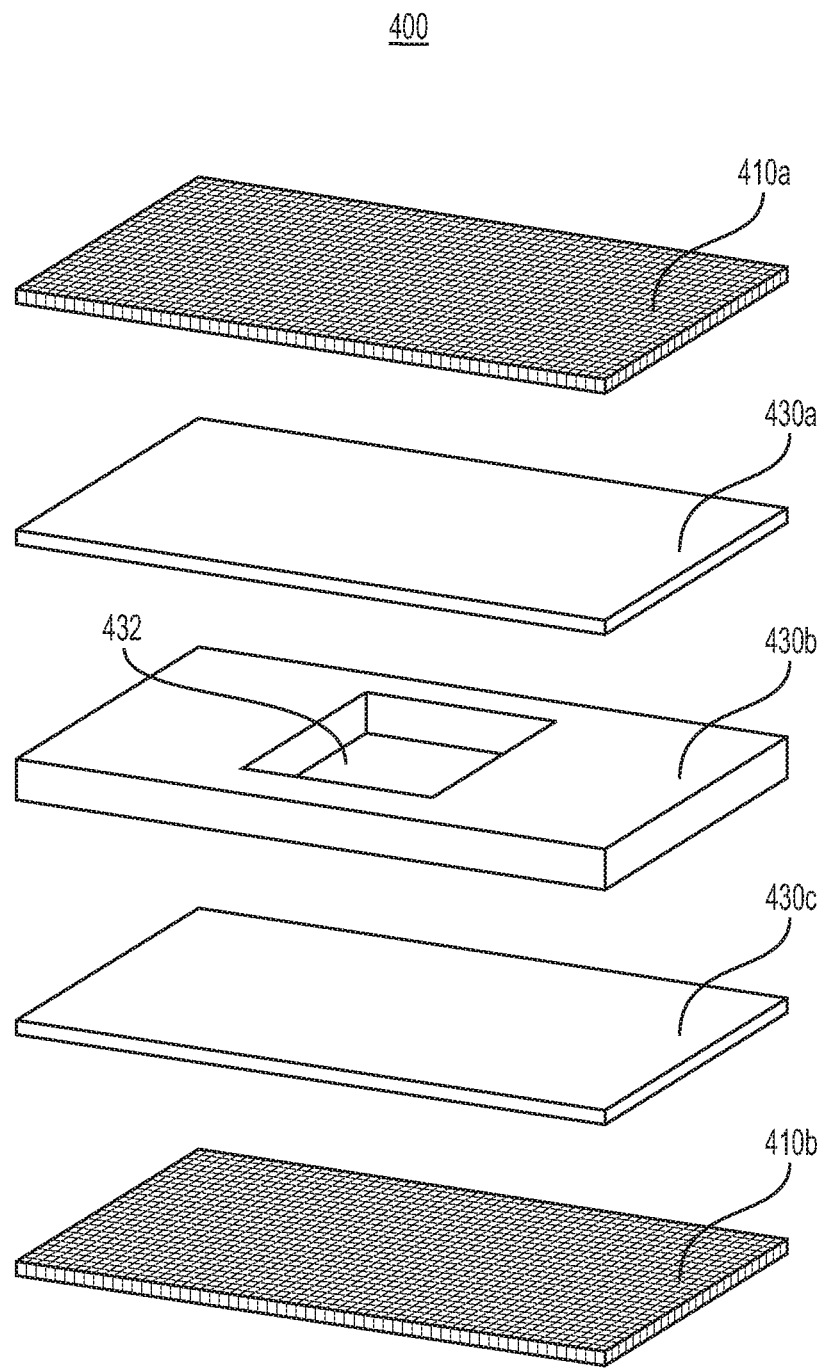
FIG. 4 is an exploded view of another capsule for an aerosol-generating device according to an example embodiment.

FIG. 4 is an exploded view of another capsule for an aerosol-generating device according to an example embodiment, wherein an inner layer of the frame defines a cavity configured to hold a compound to be heated and released. Referring to FIG. 4, a capsule 400 includes a first heater 410a, a second heater 410b, and a frame sandwiched between the first heater 410a and the second heater 410b, wherein the frame is in a form of a multi-layer structure. The multi-layer structure of the frame may include different layers configured to impart distinct flavors. As shown, the multi-layer structure of the frame includes a first frame member 430a, a second frame member 430b (which defines a cavity 432), and a third frame member 430c. The multi-layer structure of the frame of FIG. 4 may be viewed as a hybrid of the configurations in FIG. 1 and FIG. 3.

The first heater 410a and the second heater 410b may be as discussed above in connection with the first heater 110a and the second heater 110b of FIG. 1. The first frame member 430a and the third frame member 430c may be as discussed above in connection with the first frame member 330a and the third frame member 330c of FIG. 3. The second frame member 430b may be as discussed above in connection with the frame 130 of FIG. 1. The first heater 410a and the second heater 410b may be secured to the frame with any of the options discussed above. Accordingly, the relevant disclosures above will not be repeated in the interest of brevity.

Figure 5:
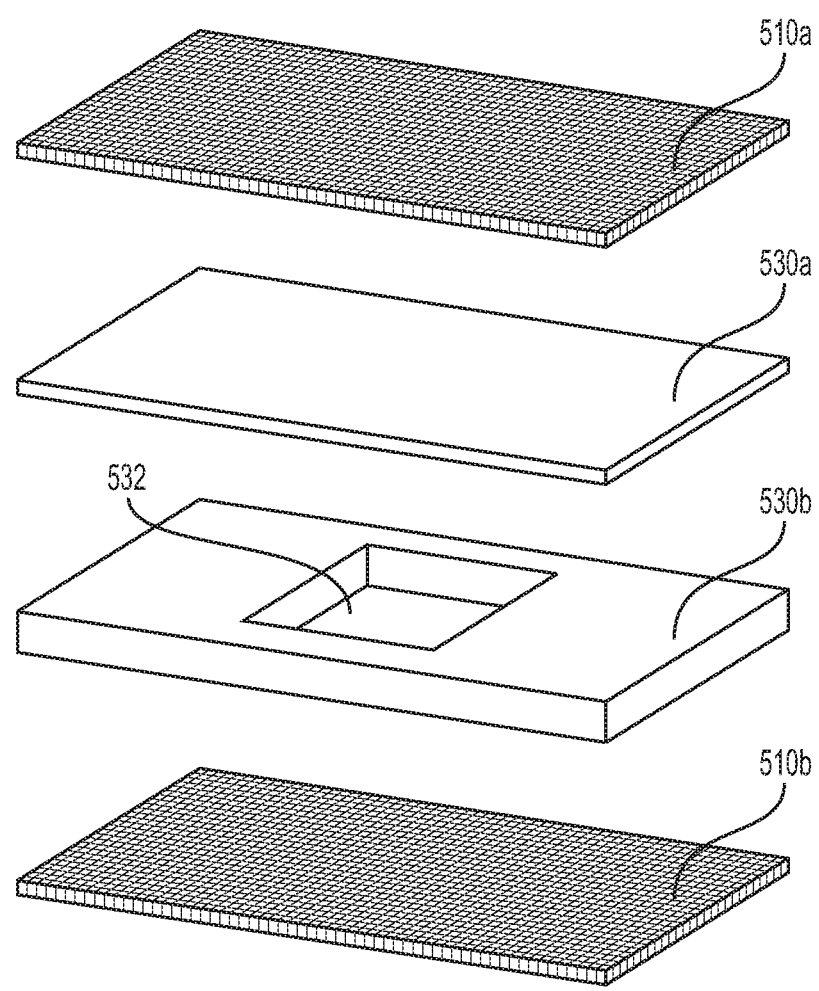
FIG. 5 is an exploded view of another capsule for an aerosol-generating device according to an example embodiment.

FIG. 5 is an exploded view of another capsule for an aerosol-generating device according to an example embodiment, wherein a layer of the frame defines a recess configured to hold a compound to be heated and released. Referring to FIG. 5, a capsule 500 includes a first heater 510a, a second heater 510b, and a frame sandwiched between the first heater 510a and the second heater 510b, wherein the frame is in a form of a multi-layer structure. As shown, the multi-layer structure of the frame includes a first frame member 530a and a second frame member 530b, which defines a cavity 532. In a non-limiting embodiment, the cavity 532 is a recess (e.g., blind hole).

The first heater 510a and the second heater 510b may be as discussed above in connection with the first heater 110a and the second heater 110b of FIG. 1. The first frame member 530a may be as discussed above in connection with the first frame member 330a of FIG. 3. The second frame member 530b may be regarded as a combination of the second frame member 430b and third frame member 430c of FIG. 4. The first heater 510a and the second heater 510b may be secured to the frame with any of the options discussed above. Accordingly, the relevant disclosures above will not be repeated in the interest of brevity.

Figure 6:
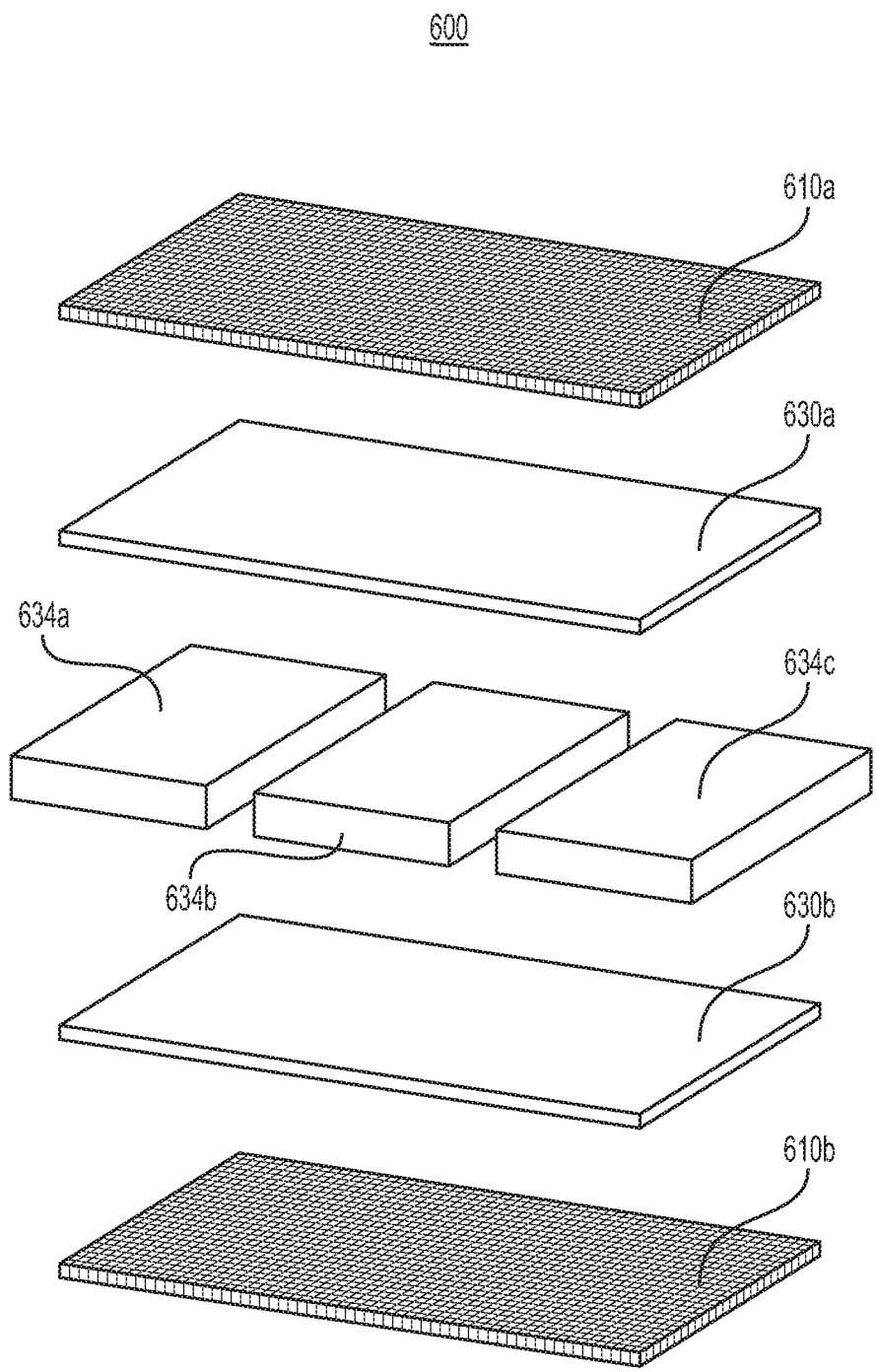
FIG. 6 is an exploded view of another capsule for an aerosol-generating device according to an example embodiment.

FIG. 6 is an exploded view of another capsule for an aerosol-generating device according to an example embodiment, wherein a layer of the frame is formed of a plurality of segments. Referring to FIG. 6, a capsule 600 includes a first heater 610a, a second heater 610b, and a frame sandwiched between the first heater 610a and the second heater 610b, wherein the frame is in a form of a multi-layer structure. As shown, the multi-layer structure of the frame includes a first frame member 630a, frame segments 634a/634b/634c, and a second frame member 630b.

The first heater 610a and the second heater 610b may be as discussed above in connection with the first heater 110a and the second heater 110b of FIG. 1. The first frame member 630a may be as discussed above in connection with the first frame member 330a of FIG. 3. The frame segments 634a/634b/634c may be regarded as segments of the frame 230 of FIG. 2. As a result, of the segments each of the frame segments 634a/634b/634c may have a different composition (e.g., of cannabinoids) and/or density to provide the desired organoleptic appeal. The first heater 610a and the second heater 610*b* may be secured to the frame with any of the options discussed above. Accordingly, the relevant disclosures above will not be repeated in the interest of brevity.

Figure 7:
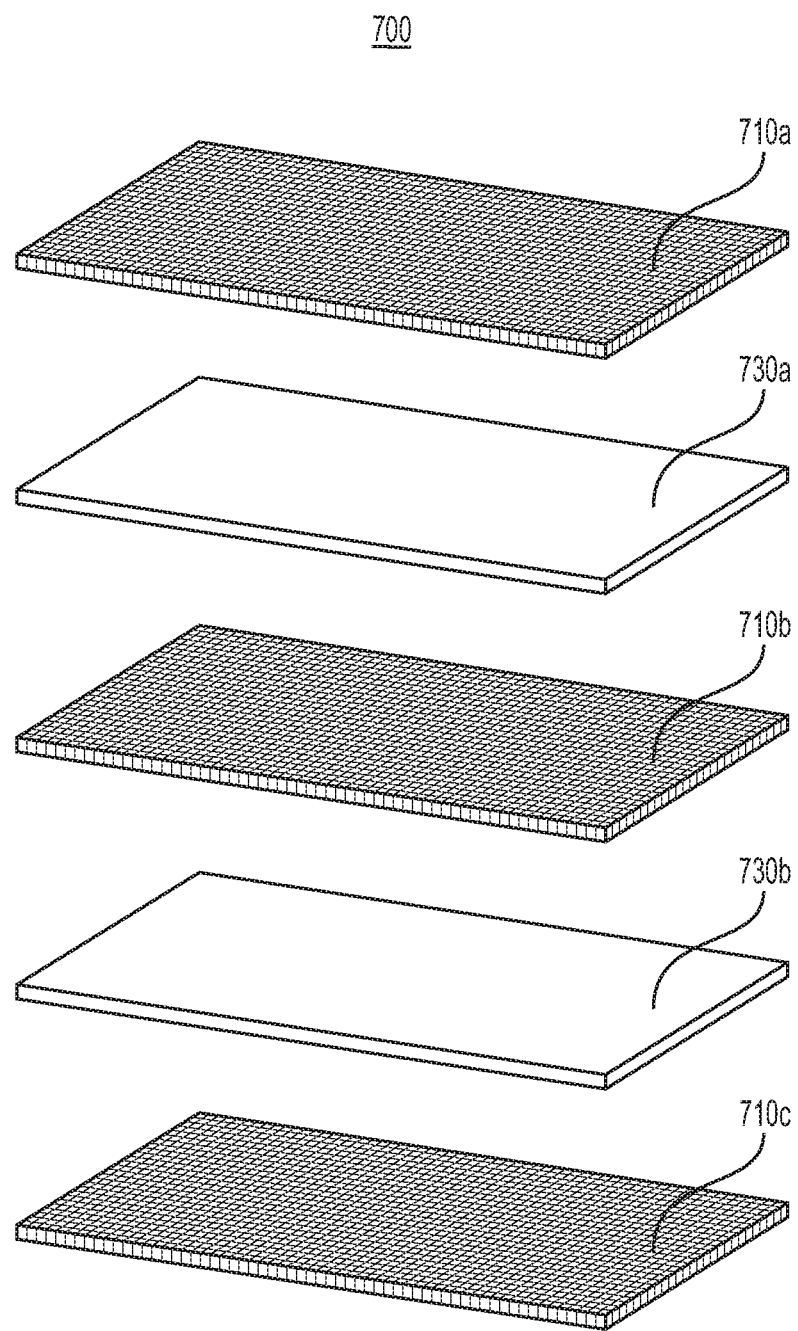
FIG. 7 is an exploded view of another capsule for an aerosol-generating device according to an example embodiment.

FIG. 7 is an exploded view of another capsule for an aerosol-generating device according to an example embodiment, wherein an inner heater is provided between adjacent layers of the frame. Referring to FIG. 7, a capsule 700 includes a first heater 710*a*, a second heater 710*b*, and a third heater 710*c*. A first frame member 730*a* is sandwiched between the first heater 710*a* and the second heater 710*b*. Additionally, a second frame member 730*b* is sandwiched between the second heater 710*b* and the third heater 710*c*.

The first heater 710*a*, the second heater 710*b*, and the third heater 710*c* may be analogous to the first heater 110*a* and the second heater 110*b* discussed in connection with FIG. 1. The first frame member 730*a* and the second frame member 730*b* may be as discussed above in connection with the first frame member 330*a* and the third frame member 330*c* of FIG. 3. The first heater 710*a*, the second heater 710*b*, and the third heater 710*c* may be secured to the frame with any of the options discussed above. Accordingly, the relevant disclosures above will not be repeated in the interest of brevity.

Figure 8:
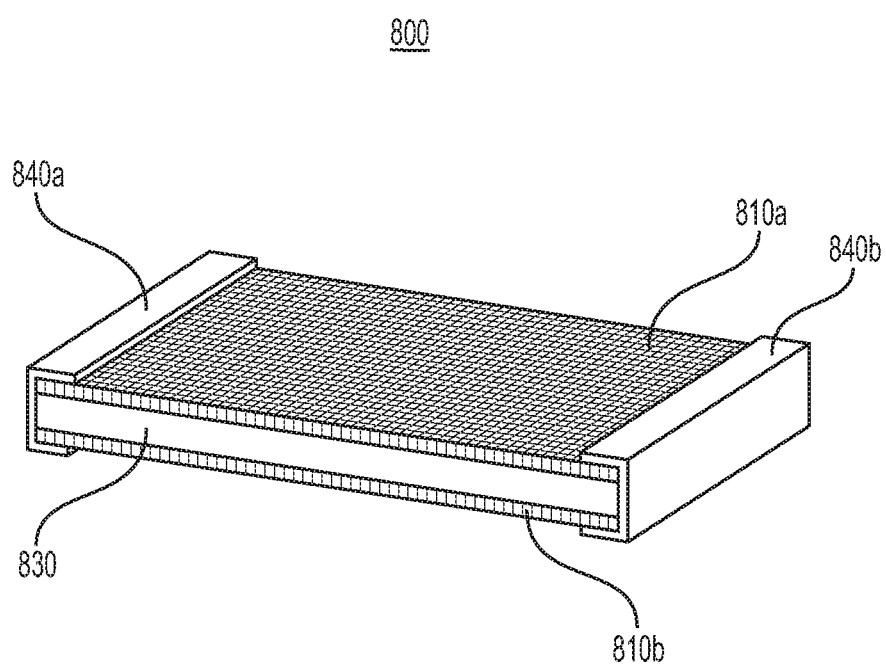
FIG. 8 is a perspective view of an assembled capsule for an aerosol-generating device according to an example embodiment.
Figure 9:
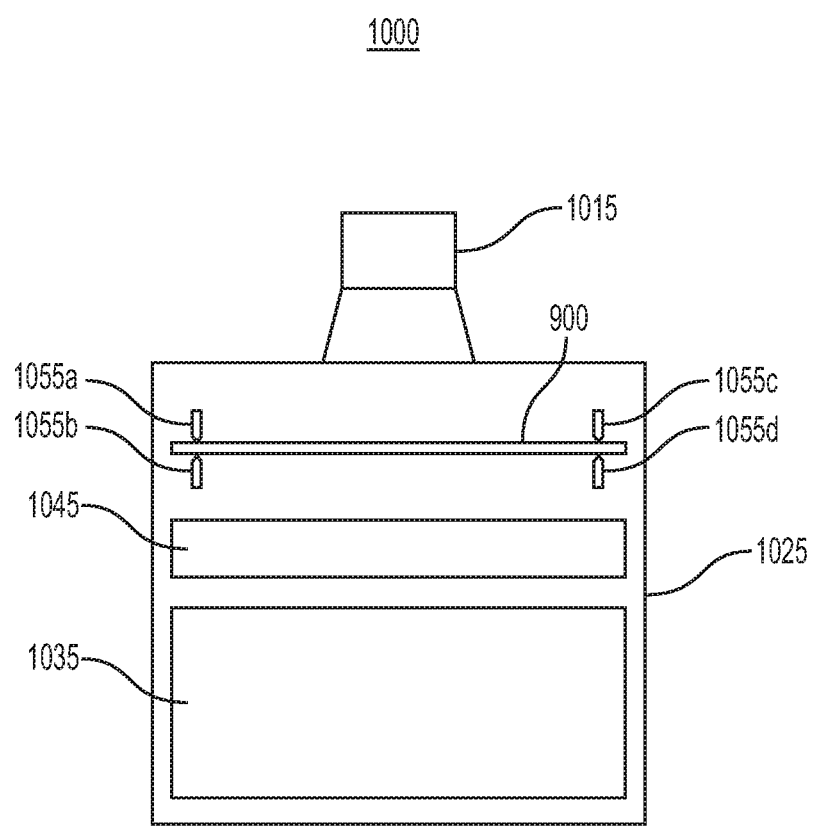
FIG. 9 is a schematic view of an aerosol-generating device according to an example embodiment.

FIG. 8 is a perspective view of an assembled capsule for an aerosol-generating device according to an example embodiment. Referring to FIG. 8, a capsule 800 includes a first heater 810*a*, a second heater 810*b*, and a frame 830 sandwiched between the first heater 810*a* and the second heater 810*b*. The first heater 810*a*, the second heater 810*b*, and the frame 830 may be as discussed above in connection with the first heater 210*a*, the second heater 210*b*, and the frame 230 of FIG. 2 and, thus, the relevant disclosure will not be repeated in the interest of brevity.

In addition, mechanical fasteners may be provided for one or more edges of the capsule 800. For instance, the mechanical fasteners may include a first clip 840*a* and a second clip 840*b*. Each of the first clip 840*a* and the second clip 840*b* may be a resilient clamping structure with a base between two spring-loaded sides/arms, although example embodiments are not limited thereto. Additionally, the first clip 840*a* and the second clip 840*b* may be formed of an insulating material (e.g., plastic). In a non-limiting embodiment, at least one of the first clip 840*a* or the second clip 840*b* may have a square U cross-section (e.g., square U cross-section with inward-leaning sides/arms when unengaged). In another non-limiting embodiment, at least one of the first clip 840*a* or the second clip 840*b* may have a triangular cross-section (wherein the sides/arms contact (or almost contact) each other when unengaged) so as to provide a greater gripping force when engaged.

At least one of the first clip 840*a* or the second clip 840*b* may also have an elongated/strip form with a length that corresponds to a majority of the length or width of capsule 800. As illustrated in FIG. 8, the first clip 840*a* and the second clip 840*b* may be provided on the two width edges of the capsule 800. However, it should be understood that the first clip 840*a* and the second clip 840*b* may additionally (or alternatively) be provided on the two length edges of the capsule 800. When assembled, the opposing sides/arms of the first clip 840*a* and the second clip 840*b* securely grip the first heater 810*a* and the second heater 810*b* to the frame 830. Furthermore, the first heater 810*a*, the second heater 810*b*, and/or the frame 830 may abut the base of the clip, although example embodiments are not limited thereto.

FIG. 9 is a schematic view of an aerosol-generating device according to an example embodiment. Referring to FIG. 9, an aerosol-generating device 1000 (e.g., heat-not-burn aerosol-generating device) may include a mouthpiece 1015 and a device body 1025. A power source 1035 and control circuitry 1045 may be disposed within the device body 1025 of the aerosol-generating device 1000. The aerosol-generating device 1000 is configured to receive a capsule 900, which may be as described in connection with any of the embodiments in FIGS. 1-8. The aerosol-generating device 1000 may also include a first electrode 1055*a*, a second electrode 1055*b*, a third electrode 1055*c*, and a fourth electrode 1055*d* configured to electrically contact the capsule 900. In an example embodiment, if the capsule 900 has a structure resembling the capsule 100 of FIG. 1, then the first electrode 1055*a* and the third electrode 1055*c* may electrically contact the first heater 110*a*, while the second electrode 1055*b* and the fourth electrode 1055*d* may electrically contact the second heater 110*b*. However, in non-limiting embodiments involving a capsule with only one heater, it should be understood that the first electrode 1055*a* and the third electrode 1055*c* (or the second electrode 1055*b* and the fourth electrode 1055*d*) may be omitted.

When the capsule 900 is inserted into the aerosol-generating device 1000, the control circuitry 1045 may instruct the power source 1035 to supply an electric current to the first electrode 1055*a*, the second electrode 1055*b*, the third electrode 1055*c*, and/or the fourth electrode 1055*d*. The supply of current from the power source 1035 may be in response to a manual operation (e.g., button-activation) or an automatic operation (e.g., puff-activation). As a result of the current, the capsule 900 may be heated to generate an aerosol. The aerosol may contain a compound (e.g., cannabinoid) that provides a medically-accepted therapeutic effect (e.g., treatment of pain, nausea, epilepsy, psychiatric disorders). Additional details of the capsule 900 and the aerosol-generating device 1000, including the mouthpiece 1015, the device body 1025, the power source 1035, the control circuitry 1045, the first electrode 1055*a*, the second electrode 1055*b*, the third electrode 1055*c*, and the fourth electrode 1055*d* as well as methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

In addition to the examples discussed herein, the medium (for the compound released with the aerosol) may be in a form of a matrix that is made of a filler material. The compound to be released may be part of an additive, such as a pre-aerosol formulation, that is introduced into the filler material. The pre-aerosol formulation may contain flavoring and/or cannabinoids.

In a non-limiting embodiment, the filler material may be processed into smaller, separate pieces (of the filler material) which are then combined to form the matrix. The processing may include cutting the filler material into pieces. For instance, the filler material may be in a form of a sheet that is cut into strips. In such an instance, the strips define interstices (interstitial spaces) that provide avenues for airflow traveling through the matrix. The sheet may have a thickness of 70 micrometers to 130 micrometers (e.g., about 100 micrometers) and an areal density (or grammage) of about 65 $g/cm^2$ to about 110 $g/cm^2$ (e.g., about 87 $g/cm^2$). The strips may have a width of about 1 mm to about 3 mm (e.g., about 2 mm), and the thickness may correspond to the thickness of the sheet from which the strips are cut. It should be understood that the values and ranges herein are not intended to be limiting and may vary depending on the embodiment.

The filler material may also be processed into smaller, separate pieces via shredding, slicing, dicing, and other suitable techniques. For instance, the filler material may be extruded into strands. In such an instance, the filler material may be in a form of a pliable (e.g., pulp-like) mass that is forced through a die to form the strands.

In another non-limiting embodiment, in lieu of (or in addition to) processing the filler material into separate pieces, one or more of the filler materials may be folded, bunched, crumpled, and/or otherwise combined in a compressed manner to form the matrix. In such an instance, the creases of the filler material(s) may define the interstices through which air flows through the matrix. In an example embodiment, the filler material may be processed so that the pieces (e.g., via cutting) of a filler material are combined with another filler material that is folded, bunched, and/or crumpled (and not cut) in order to form the matrix.

The filler material of the matrix may also be a mesh or other porous material. In such an example embodiment, an average pore size may be about 10-12 micrometers (e.g., about 11 micrometers). Optionally, the filler material (e.g., if in a form of a non-porous or low porosity sheet) may be perforated to increase a porosity and/or flow paths through the filler material for the matrix.

The filler material and resulting matrix may be a composite material made from *cannabis* and/or non-*cannabis* materials. The matrix may be provided with or without flavors or a flavoring system. The matrix may also be provided with or without cannabinoids. Furthermore, the filler material may be a flat, continuous, and sheet-like material that is processed and/or stored as a roll for convenience. The roll may optionally include a mandrel around which the filler material is wound. Alternatively, the filler material may be a block of material, an extruded material, or a material that is in a shape other than a flat sheet.

In an example embodiment, the filler material is a non-*cannabis* cellulose. The non-*cannabis* cellulose may be cast or made into the filler material so as to have a sheet-like (e.g., paper-like) form. The non-*cannabis* cellulose may include a *cannabis* extract. In one instance, the non-*cannabis* cellulose is a water-insoluble organic polymer material that may be made from plant material (e.g., wood, cotton), plant-based material, plant cell walls, vegetable fibers, polysaccharide, chains of glucose units (monomers), cellulose acetate, combinations or sub-combinations of these materials, etc. In another instance, the non-*cannabis* cellulose is partially water-soluble and made from the same materials, or combinations, or sub-combinations, of the materials, etc.

The filler material may be about 30% to 99% alpha-cellulose material made from plant material and about 0.01% to 2% ash, with a remainder being hemicellulose. The hemicellulose may be a plant-based material that includes beta-cellulose, gamma-cellulose, biopolymers, or combinations, or sub-combinations, thereof. The primary strength and water-insoluble properties of the filler material may be derived from the content of alpha-cellulose within the filler material. In an example embodiment, the filler material is water-insoluble and is more than 98% alpha-cellulose material made from plant material and about 0.01% to 2% ash, with the remainder being hemicellulose. It should be understood that the values and ranges herein are not intended to be limiting and may vary based on the embodiment.

In another example embodiment, the filler material is a *cannabis* cellulose. The *cannabis* cellulose may be cast or made into the filler material so as to have a sheet-like (e.g., paper-like) form. The *cannabis* cellulose may or may not include *cannabis* extract. The *cannabis* cellulose may be a water-insoluble material or, alternatively, a partially water-soluble material.

The filler material may be about 30% to 99% *cannabis* cellulose and about 0.01% to 2% ash, with the remainder being hemicellulose. In an example embodiment, the filler material is water-insoluble and is more than 98% *cannabis* cellulose and about 0.01% to 2% ash, with the remainder being hemicellulose. It should be understood that values and ranges herein are not intended to be limiting and may vary based on the embodiment.

A flavoring, a flavorant, or a flavor system may be included in the filler material of the matrix in order to release flavors and/or an aroma (e.g., upon heating and/or when an airflow passes through the matrix). For instance, the flavoring may include volatile *cannabis* flavor compounds. The flavoring may also include other flavor compounds instead of (or in addition to) the *cannabis* flavor compounds.

The flavoring may be at least one of a natural flavorant, an artificial flavorant, or a combination of a natural flavorant and an artificial flavorant. For instance, the at least one flavorant may include menthol, wintergreen, peppermint, cinnamon, clove, combinations thereof, and/or extracts thereof. In addition, flavorants may be included to provide herb flavors, fruit flavors, nut flavors, liquor flavors, roasted flavors, minty flavors, savory flavors, combinations thereof, and any other desired flavors.

A flavoring may be added to the filler material before, during, and/or after the filler material is fabricated (e.g., made into a sheet-like structure). The flavoring may also be added before and/or after the filler material is divided into pieces (e.g., cut into strips). In one instance, the flavoring is added (e.g., infused) before and/or during an initial formation of the filler material. Additionally (or alternatively), after the formation of the filler material, the addition of the flavoring may be accomplished by dipping the filler material and/or pieces into the flavoring, dispersing the flavoring onto the filler material and/or pieces, or otherwise exposing the filler material and/or pieces to the flavoring. In another instance, the filler material and/or pieces are left unflavored such that flavoring is not included in the matrix.

The matrix within a capsule may include about 1-15 mg of a compound that will be in the generated aerosol. In particular, the matrix may be designed to contain enough of the compound such that the initial (first) five draws from the matrix includes about 100-500 micrograms of the compound per draw. In an example embodiment, a "draw" is about 55 $cm^3$ of fluid (e.g., ambient air and aerosol) that flows for about 3-5 seconds from or through the capsule.

Cannabinoids may be added to the filler material before, during, and/or after the filler material is fabricated (e.g., made into a sheet-like structure). The cannabinoids may also be added before and/or after the filler material is divided into pieces (e.g., cut into strips). In one instance, the cannabinoids are added (e.g., infused) before and/or during an initial formation of the filler material. Additionally (or alternatively), after the formation of the filler material, the addition of the cannabinoids may be accomplished by spraying or dipping the filler material and/or pieces into the cannabinoids, dispersing the cannabinoids onto the filler material and/or pieces, or otherwise exposing the filler material and/or pieces to the cannabinoids.

The flavoring and/or cannabinoids may be included in a pre-aerosol formulation, which is infused into the filler material. Alternatively, the pre-aerosol formulation may be separate from the flavoring and/or cannabinoids and, thus, separately infused into the filler material.

The pre-aerosol formulation may include at least one aerosol former. Suitable aerosol formers include diols (e.g., propylene glycol and/or 1,3-propanediol), glycerin, combinations, or sub-combinations thereof. Various amounts of the aerosol former may be used. For instance, the aerosol former may be included in an amount ranging from about 20% to 90% by weight based on the weight of the pre-aerosol formulation (e.g., about 50% to 80%, about 55% to 75%, about 60% to 70%). In addition, the pre-aerosol formulation may include a weight ratio of the diol to glycerin that ranges from about 1:4 to 4:1 (e.g., about 3:2), although example embodiments are not limited thereto.

The pre-aerosol formulation may include water in an amount ranging from about 5% to 40% by weight based on the weight of the pre-aerosol formulation (e.g., about 10% to 15%), although example embodiments are not limited thereto. In addition, the remaining portion of the pre-aerosol formulation that is not water (and cannabinoids and/or flavoring compounds) may be an aerosol former. In a non-limiting embodiment, the aerosol former is about 30% to 70% by weight propylene glycol, with the balance being glycerin.

The pre-aerosol formulation may include a flavorant in an amount ranging from about 0.2% to 15% by weight (e.g., about 1% to 12%, about 2% to 10%, about 5% to 8%). In addition, the pre-aerosol formulation may include a compound (that will be in the generated aerosol) in an amount ranging from about 1% to 10% by weight (e.g., about 2% to 9%, about 2% to 8%, about 2% to 6%). The pre-aerosol formulation may also include 10-15% by weight water, with the remaining portion of the pre-aerosol formulation (that is not a flavorant or the compound) being a mixture a diol and glycerin at a ratio from about 2:3 to 3:2 by weight.

The matrix discussed herein is described in more detail in U.S. application Ser. No. 16/125,293, filed Sep. 7, 2018, titled "CAPSULE CONTAINING A MATRIX, DEVICE WITH THE MATRIX, AND METHOD OF FORMING THE MATRIX," disclosure of which is incorporated herein in its entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:
a first heater;
a second heater, each of the first heater and the second heater being a permeable, singular, and continuous structure;
a frame sandwiched between the first heater and the second heater, the frame defining open spaces therein and having a rigidity that is adequate to support the first heater and the second heater, the open spaces within the frame being interconnected and sized for aerosol-permeability and capillary action, the capsule structured to facilitate a through flow of air via the first heater, the frame, and the second heater; and
a cannabinoid-containing material.

2. The capsule of claim 1, wherein at least one of the first heater or the second heater is in a form of a mesh.

3. The capsule of claim 1, wherein at least one of the first heater or the second heater is in a form of a perforated foil.

4. The capsule of claim 1, wherein the frame has a density between 0.454 g/cm$^3$ to 1.361 g/cm$^3$.

5. The capsule of claim 1, wherein the frame defines a cavity.

6. The capsule of claim 5, wherein the cavity is a through-hole.

7. The capsule of claim 5, further comprising:
an aerosol-forming substrate in the cavity of the frame, the aerosol-forming substrate including the cannabinoid-containing material and configured to produce an aerosol when heated by at least one of the first heater or the second heater.

8. The capsule of claim 7, wherein the cannabinoid-containing material includes a fibrous material configured to release a compound as part of the aerosol.

9. The capsule of claim 1, wherein the frame is non-conductive and electrically isolates the first heater and the second heater.

10. The capsule of claim 1, wherein the frame is in a form of a multi-layer structure.

11. The capsule of claim 10, wherein the multi-layer structure of the frame includes different layers configured to impart distinct flavors.

12. The capsule of claim 10, further comprising:
a third heater within the multi-layer structure of the frame.

13. The capsule of claim 1, wherein the frame is formed of sintered particles.

14. The capsule of claim 1, wherein the frame is formed of consolidated fibers.

15. The capsule of claim 14, wherein the consolidated fibers of the frame are plant-based fibers.

16. The capsule of claim 15, wherein the plant-based fibers are cannabis fibers.

17. The capsule of claim 16, wherein the cannabis fibers include at least one of tetrahydrocannabinolic acid (THCA) or tetrahydrocannabinol (THC).

18. The capsule of claim 16, wherein the cannabis fibers include at least one of cannabidiolic acid (CBDA) or cannabidiol (CBD).

19. An aerosol-generating device, comprising:
a device body;
the capsule of claim 1, the device body configured to receive the capsule;
a plurality of electrodes within the device body and configured to electrically contact the first heater and the second heater of the capsule; and
a power source configured to supply an electric current to the first heater and the second heater of the capsule via the plurality of electrodes.

20. A method of generating an aerosol, comprising:
electrically contacting a plurality of electrodes with the capsule of claim 1; and
supplying an electric current to the first heater and the second heater of the capsule via the plurality of electrodes.

* * * * *